United States Patent [19]

Panek et al.

[11] Patent Number: 4,575,559

[45] Date of Patent: Mar. 11, 1986

[54] PROCESS FOR PREPARING CERTAIN SULFOPHENETHYLSILOXANES

[75] Inventors: Edward J. Panek, Randolph Township, Dover County, N.J.; Thomas M. Schmitt, Dearborn Heights; Pauls Davis, Gibraltar, both of Mich.; Jen-Sheng Ku, Grosse Ile, Mich.

[73] Assignee: BASF Wyandotte Corporation, Wyandotte, Mich.

[21] Appl. No.: 700,645

[22] Filed: Feb. 12, 1985

[51] Int. Cl.$^4$ .............................. C07F 7/08; C07F 7/18
[52] U.S. Cl. .................................................. 556/428
[58] Field of Search ........................................ 556/428

[56] References Cited

U.S. PATENT DOCUMENTS 4,042,612  8/1977  Magee .................................. 556/428
4,203,914  5/1980  Finke et al. ......................... 556/428

Primary Examiner—Paul F. Shaver
Attorney, Agent, or Firm—David L. Hedden; Joseph D. Michaels

[57] ABSTRACT

This invention relates to a process for preparing certain sulfophenethylsiloxanes by reacting nearly equimolar amounts of chlorosulfonic acid with certain phenethyltrichlorosilanes in the presence or absence of a solvent according to the specified reaction conditions.

11 Claims, No Drawings

PROCESS FOR PREPARING CERTAIN SULFOPHENETHYLSILOXANES

BACKGROUND OF THE INVENTION

1. Field of the Invention

This invention relates to a process for preparing certain sulfophenethylsiloxanes by reacting essentially equimolar amounts of chlorosulfonic acid with certain phenethyltrichlorosilanes optionally in the presence of a solvent according to specified reaction conditions.

2. Description of the Prior Art

It is known to prepare sulfophenethylsiloxanes by the reaction of chlorosulfonic acid and a phenethyltrichlorosilane. U.S. Pat. No. 2,968,643 describes such a reaction in Example 1 of the patent. However, this example uses an excess of chlorosulfonic acid to form the water insoluble intermediate. This process also creates environmental problems because it is necessary to dispose the by-products generated in this process.

SUMMARY OF THE INVENTION

This invention relates to a process for preparing a sulfophenethylsiloxane having either of the following formulae:

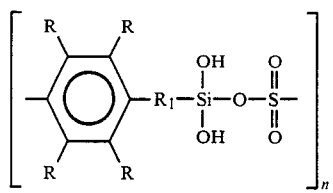
(I)

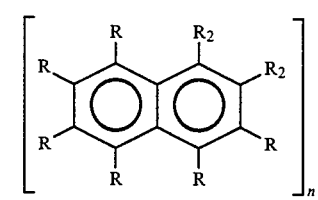
(II)

comprising:
(a) adding chlorosulfonic acid and a phenethyltrichlorosilane having either of the following formulae:

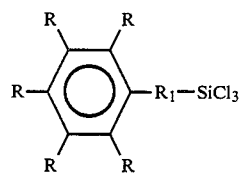
(III)

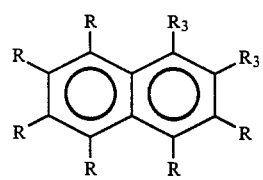
(IV)

in essentially equimolar ratios of chlorosulfonic acid and phenethyltrichlorosilane to a reaction vessel;
(b) heating the reaction mixture of (a) to a temperature greater than 45° C., preferably 80° C. to 100° C., until the evolution of hydrogen chloride is substantially complete; and
(c) hydrolyzing the reaction mixture;
wherein R of Formulae I, II, III, and IV is individually hydrogen, halogen, or an alkyl radical having 1-4 carbon atoms; $R_1$ is an alkylene radical having 2 to 5 carbon atoms; $R_2$ is R or

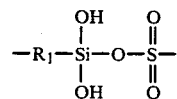

with the proviso that at least one $R_2$ be

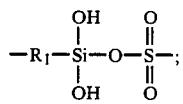

$R_3$ is R or $-R_1-SiCl_3$ with the proviso that at least one $R_3$ be $-R_1SiCl_3$; and n is at least 1. $R_1$ is an alkylene radical having 2 to 5 carbon atoms; and n is at least 1, preferably 2 to 4.

The process may also be carried out in the presence of a solvent. This offers the advantage of easier handling of the reactants, but increases the material costs. If the process is carried out in the presence of a solvent, the reaction mixture is preferably heated to a temperature sufficient to reflux the solvent; and the intermediate is preferably cooled after the evolution of hydrogen chloride is substantially complete. The product is then recovered by conventional means such as distillation of the solvent and filtration. If no solvent is used, the intermediate can be heated before hydrolysis.

The process is particularly significant because essentially equimolar ratios of chlorosulfonic acid and phenethyltrichlorosilane are used. This is evidently possible because the chemistry of the process requires that preferably two moles of hydrogen chloride is driven off before hydrolyzing. Failure to do so results in an incomplete reaction and the formation of insoluble by-products.

The subject process produces practically no waste and therefore minimal environmental problems since it does not produce aqueous sulfuric acid and hydrochloric acid. Also, it is possible to achieve yields of more than 98 percent on a regular basis when using the subject process.

The uses of the subject compounds are well known, particularly as silicate stabilizers in antifreeze formulations.

DESCRIPTION OF THE PREFERRED EMBODIMENTS

The phenethyltrichlorosilane compounds having structural formulae III or IV are well known in the art. Generally preferred are compounds wherein R is a hydrogen atom and $R_1$ is an ethylene or propylene radical. Specific examples of such compounds are β-phenethyltrichlorosilane and α-phenethyltrichlorosilane.

The phenethyltrichlorosilane and the chlorosulfonic acid are added to a reaction vessel in essentially equimolar ratios (preferably 1:1 to 1:1.05). A solvent which will not react with the chlorosulfonic acid or the phenethyltrichlorosilane may also be used and added to dilute the reaction medium. Such solvents include aliphatic hydrocarbons and their halogenated derivatives. Specific examples include 1,1,2-trichloro-1,2,2-trifluoroethane, 1,2-difluoro-1,1,2,2-tetrachlororoethane, 1,2-dichloroethane, 1,1,2-trichloroethane, and heptane. In general it is preferable to add the chlorosulfonic acid and the phenethyltrichlorosilane at a temperature of less than 45° Celsius, preferably 80° C. to 100° C.

After adding the reactants and the solvent, if one is used, to the reaction vessel, the reaction mixture is heated to a temperature of at least 45° C., or when a solvent is used to a temperature sufficient to reflux the solvent, until the evolution of hydrogen chloride is substantially complete to form an intermediate. By substantially complete, it is meant that preferably at least 95 percent of the theoretically calculated hydrogen chloride should have evolved, most preferably at least 98 percent. Preferably one mole of HCl should evolve per mole of reactant, i.e., two moles of HCl should evolve if one mole of silane and one mole of chlorsulfonic acid are used. It is important that the hydrogen chloride evolution be substantially complete even if a solvent has not been used. Otherwise insoluble by-products are likely to form. The intermediate can be cooled if a solvent is used. Then the intermediate preferably is hydrolyzed to form the end product. The final product is then recovered by filtering from diluent or other means if a solvent is not used.

EXAMPLE 1

This example will illustrate the addition of chlorosulfonic acid to phenethyltrichlorosilane in the absence of a solvent.

To a stirred reaction vessel containing 359.4 g (1.50 moles) of β-phenethyltrichlorosilane at a temperature of 45° C. to 50° C., 174.8 g (150 moles) of chlorosulfonic acid were added from an addition funnel over a period of approximately four hours during which time hydrogen chloride was generated.

The mixture was then reacted for an additional 60 minutes during which time HCl evolution ceased and the mixture became solid. Then two portions were heated to 94° C. for 4½ hours in the presence of moisture to form the final product.

Examples 2–6 illustrate the use of a solvent in the subject process.

In these examples, the reactions were run in a four-necked round bottom flask equipped with a paddle stirrer and variable speed motor, heating mantle, thermowell and thermometer, one or two addition funnels, and a high efficiency double wall reflux condenser. The off-gas from the reflux condenser went to a scrubber for the capture and automatic titration of the liberated hydrogen chloride. The reservoir of the scrubber was a four-necked round bottom flask which contained water maintained at pH 9.0 by an automatic buret fitted with a 20 ml glassware unit filled with 50 percent sodium hydroxide controlled by an end point titrator. A pH electrode and the buret tip were fitted into a rubber stopper which was placed in one of the flask necks. The other three necks contained the off-gas inlet, the circulation pump inlet line which extended to the bottom of the flask, and a Vigreux column through which the pump output cascaded downwards.

EXAMPLE 2

This example will illustrate the addition of the chlorosulfonic acid to the solvent and chlorophenethyltrichlorosilane.

To a reaction vessel, 200 ml 1,2-dichloroethane and 68.4 g (0.25 mole) chlorophenethyltrichlorosilane were added. Then 29.1 g (0.25 mole) of chlorosulfonic acid was added to the cooled, rapidly stirred solution over a period of eight minutes. The temperature was then raised from 20° C. to the reflux temperature (82° C.) and held for three hours. During this time more HCL was evolved and the intermediate separated from the solution as an oatmeal-like precipitate. The precipitate was separated by vacuum filtration using a Buchner funnel fitted with a fine porosity glass frit. The solids were placed in a large porcelain evaporating dish on a steam bath. Twenty ml deionized water was added to speed hydrolysis. After overnight reaction, 63 g of solid were recovered, with a silicon dioxide content of 21.4 percent. The yield of isolated product was thus 90 percent. The spectra, the acidity, and the solubility behavior supported the structure of the product as chlorosulfophenethylsiloxane.

EXAMPLE 3

This example will illustrate the simultaneous addition of the chlorosulfonic acid and the phenethyltrichlorosilane.

To a reaction vessel, 130 ml 1,1,2-trichloro-1,2,2-trifluoroethane was added and heated to reflux temperature (48° C.). Then 120.0 g (0.50 mole) of β-phenethyltrichlorosilane from one addition funnel and 61.2 g (0.525 mole) of chlorosulfonic acid from a second addition funnel were added to the solvent accompanied by rapid stirring over a period of 15 minutes.

Reflux was maintained for sixty additional minutes, during which time HCl evolution ceased and a large amount of solid separated from solution. One liter of water was added and the chlorofluorocarbon solvent was removed by azeotropic distillation. Most of the solid dissolved in the water. The final volume of water was adjusted to one liter and a 170 ml aliquot was centrifuged to remove insolubles and then evaporated to dryness on a steam bath (162 ml yielded 22.5 g). The solid isolated by centrifugation weighed between 0.1 to 0.2 g which indicated there was approximately one percent water insoluble material. Based on the evaporation experiment the yield of product was 139.0 g. The exact yield was unknown since the $SiO_2$ content was not determined. If a $SiO_2$ content of greater than 20.5 percent is assumed, the yield was greater than 95 percent. The infrared spectrum, solubility, and acid equivalent weight (220 g/mole) indicated the product was β-sulfophenethylsiloxane.

EXAMPLE 4

This example will illustrate the addition of the chlorosulfonic acid to the solvent and napthylethyltrichlorosilane.

To a reaction vessel, 200 ml 1,2-dichloroethane and 73 g (0.25 mole) napthylethyltrichlorosilane are added. Then, 29.1 g (0.25 mole) of chlorosulfonic acid are added to the cooled, rapidly stirred solution over a period of eight minutes. The temperature is raised from 20° C. to the reflux temperature (82° C.) and held for three hours. During this time more HCl is evolved and the intermediate separated from the solution as an oatmeal-like precipiate. The precipitate is separated by vacuum filtration using a Buchner funnel fitted with a fine porosity glass frit. The solids are placed in a large porcelain evaporating dish on a steam bath. Twenty ml deionized water is added to speed hydrolysis. After overnight reaction, 63 g of solid is recovered, with a silicon dioxide content of 21.4 percent. The yield of isolated product is comparable to Example 2. The product is identified to be sulfonaphtylethylsiloxane.

EXAMPLE 5

In this example, the β-phenethyltrichlorosilane was added to a reaction vessel containing the solvent and chlorosulfonic acid.

In a reaction vessel, 120 ml of 1,2-difluoro-1,1,2,2,-tetrachloroethane and 58.3 g (0.50 mole) of chlorosulfonic acid were added. Then 120.0 g (0.50 mole) of β-phenethyltrichlorosilane were added to the rapidly stirred suspension over a period of 32 minutes at room temperature (0.32 mole hydrogen chloride liberated). The heater was turned on and the temperature was brought up to reflux (86° C.) within 25 minutes. During this heat-up, rapid hydrogen chloride evolution occurred with precipitation of solid product. A total of 0.92 mole of hydrogen chloride was liberated. The reaction mixture was cooled and one liter of water was added. Most of the solid dissolved. The organic solvent was removed by azeotropic distillation (110 ml recovered). The hazy water solution was filtered (Whatman #30 paper) and evaporated on a steam bath to yield 114 g of product. The exact yield was unknown since the silicon dioxide content was not determined. If a silicon dioxide content of 23 percent is assumed, the yield was 87 percent.

EXAMPLE 6

This example illustrates the addition of the chlorosulfonic acid to the solvent and β-phenethyltrichlorosilane.

In a reaction vessel, 500 ml of 1,2-dichloroethane and 120.0 g (0.50 mole) of β-phenethyltrichlorosilane were added. Then 58.3 g (0.50 mole) of chlorosulfonic acid was added to the rapidly stirred solution over a period of five minutes. The temperature was increased to 82° C. over a period of 90 minutes. Hydrogen chloride evolution (1.01 mole) was complete in 230 minutes. Water (18.0 g, 1.0 mole) was added dropwise over a period of 14 minutes. An additional 0.99 mole of hydrogen chloride was evolved during the water addition (complete hydrogen chloride evolution requires one mole of water). The reaction mixture changed from a clear solution before water addition to a slurry with an oatmeal-like appearance midway through the water addition to a slurry of solid product particles at the end of the water addition.

The crude product was isolated by vacuum filtration using a Buchner funnel with a coarse glass frit. The crude product (ca. 300 g) was dried to constant weight (124.3 g) on a steam bath. (The excess weight in the crude product is mainly occluded solvent; a typical solvent recovery from the filtration is 65 percent). The silicon dioxide content of this product was 22.9 weight percent which means the yield of isolated product was 95 percent. The spectra, complete water solubility, and acid equivalent weight (240 g/mole) were consistent with β-sulfophenethylsiloxanes.

COMPARISON EXAMPLE

This example illustrates the use of excess chlorosulfonic acid without a solvent. In this example, 1005.6 g. (8.63 mole) of chlorosulfonic acid and 1034.1 g. (4.31 moles) of β-phenethyltrichlorosilane were used. The addition temperature was 50° C. The reactants were added over a one hour period and it took an additional one hour for the hydrogen chloride to evolve.

The reaction mixture was hydrolyzed with ice and water (in a one-to-one mixture) with rapid stirring. A rapidly settling granular product was obtained. The upper layer was decanted and the product filtered off. The filter cake was washed until neutral with approximately 15 liters of chilled distilled water. The filter cake was dried with suction and transferred to a twelve-liter evaporating dish (about 2700 g. of filter cake). The product was then hydrolyzed on a steam bath with 4 liters of distilled water. After a clear solution was obtained, the dilute hydrochloric acid formed was evaporated on a steam bath (about 3 days) until a constant weight was obtained and no $Cl^-$ could be detected in the product by the $AgNO_3$ test.

The final yield was 950.0 g. which was 77 percent of theory based upon a 21 percent $SiO_2$ content.

The examples herein illustrate that improved yields of β-sulfophenethylsiloxanes can be obtained without stress to the environment by using essentially equimolar amounts of chlorosulfonic acid and β-phenethyltrichlorosilane at specified reaction conditions. The comparison example shows that a lower yield results when excess chlorosulfonic acid is used. This process is also wasteful and causes stress in the environment because of the large amounts of by-products created. Specifically, one mole each of sulfuric acid and hydrochloric acid are formed for each mole of excess chlorosulfonic acid. These must be removed from the product. Since the product itself is water-soluble, some product is dissolved and washed away at the same time. Thus the yield is lower, and the waste water contains not only inorganic acids, but also organic compounds which raise the total organic carbon content of the effluent.

The embodiments of the invention in which an exclusive privilege or property is claimed are defined as follows:

1. A process for preparing a sulfophenethylsiloxane having either of the following formulae:

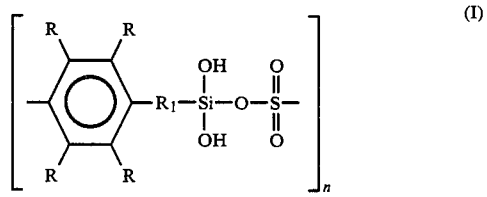

(I)

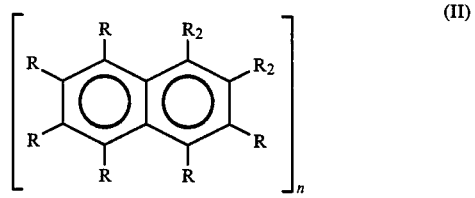

(II)

comprising:
(a) adding chlorosulfonic acid and a phenethyltrichlorosilane having either of the following formulae:

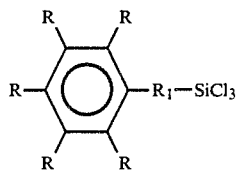
(III)

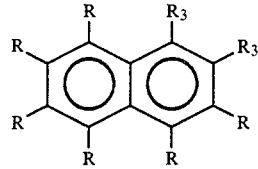
(IV)

in essentially equimolar ratios of chlorosulfonic acid and phenethyltrichlorosilane to a reaction vessel;

(b) heating the reaction mixture to a temperature greater than 45° C. until the evolution of hydrogen chloride is substantially complete to form an intermediate; and (c) hydrolyzing the intermediate;

wherein R of Formulae I, II, III, and IV is individually hydrogen, halogen, or an alkyl radical having 1 to 4 carbon atoms; $R_1$ is an alkylene radical having 2 to 5 carbon atoms; $R_2$ is R or

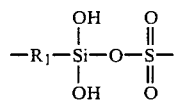

with the proviso that at least one $R_2$ be

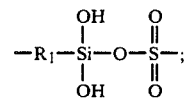

$R_3$ is R or —$R_1$—$SiCl_3$ with the proviso that at least one $R_3$ be —$R_1SiCl_3$; and n is at least 1.

2. The process of claim 1 wherein n is 2 to 4.

3. The process of claim 2 wherein the intermediate is heated during hydrolysis.

4. The process of claim 2 wherein the reaction is carried out in the presence of a solvent, and the product is recovered from the solvent.

5. The process of claim 4 wherein the intermediate is cooled prior to hydrolysis.

6. The process of claim 5 wherein the phenethyltrichlorosilane is β-phenethyltrichlorosilane.

7. The process of claim 6 wherein the solvent is selected from the group consisting of 1,2-dichloroethane, 1,1,2-trichloroethane, and 1,2-difluoro-1,1,2,2-tetrachloroethane.

8. The process of claim 7 wherein the chlorosulfonic acid and β-phenethyltrichlorosilane are added to a reaction vessel simultaneously.

9. The process of claim 8 wherein the amount of β-phenethyltrichlorosilane used is a 5 percent excess based upon the chlorosulfonic acid.

10. The process of claim 7 wherein the chlorosulfonic acid is added to the β-phenethyltrichlorosilane.

11. The process of claim 7 wherein the β-phenethyltrichlorosilane is added to the chlorofulsonic acid.

* * * * *